US00PP10891P

United States Patent [19]

Blythe

[11] Patent Number: Plant 10,891

[45] Date of Patent: May 11, 1999

[54] LANTANA PLANT NAMED 'MONGEN'

[75] Inventor: Eugene Blythe, LaVerne, Calif.

[73] Assignee: Monrovia Nursery Company, Azusa, Calif.

[21] Appl. No.: 08/933,232

[22] Filed: Sep. 18, 1997

[51] Int. Cl.[6] ..... A01H 5/00

[52] U.S. Cl. ..... Plt./227

[58] Field of Search ..... Plt./54.1, 68.1, Plt./227

[56] References Cited

U.S. PATENT DOCUMENTS

P.P. 7,626 8/1991 Sweeney ..... Plt./54.

*Primary Examiner*—Douglas W. Robinson
*Assistant Examiner*—Kent L. Bell

[57] ABSTRACT

A new and distinct selection of trailing Lantana which shal be referred hereinafter as *Lantana sellowiana* cultivar 'Mon gen'. *Lantana sellowiana* cultivar 'Mongen' differs distinc tively from other *Lantana sellowiana* plants by its uniqu variegated leaves and slower growth habit.

1 Drawing Sheet

BACKGROUND OF THE INVENTION

This invention relates to a new and distinct selection of *Lantana sellowiana*, LINK & OTTO native to South America and a member of the Verbenaceae family. *Lantana sellowiana* cv. 'Mongen' was not a result of a specific breeding program. My selection was found as a branch mutation on a vegetatively propagated *Lantana sellowiana* plant. I discovered this branch in October 1993 at Montrovia Nursery Company at 18331 E. Foothill Boulevard. Azusa, Calif. Selection was based on the attribute of the variegated foliage. My new plant has been asexually reproduced by cuttings since the discovery in 1993 at Monrovia Nursery at 18331 E. Foothill Boulevard, Azusa, Calif. Had this chance branch mutation not been discovered and propagated, it may have been lost to mankind. It is unlikely these particular select and favorable attributes of this plant could be conveyed to progeny through sexual reproduction in the next generation. However, through extensive propagation by rooting of the plant it has been established that the novel exceptional characteristics of this plant are stable and reliably passed on to clonal specimens through asexual reproduction.

SUMMARY OF THE INVENTION

*Lantana sellowiana* cultivar 'Mongen' was noticed and selected because of the attractive yellow and green variegated foliage.

Comparison of other Selections

The parent of my new selection exhibits solid darker green foliage and a low spreading habit. The overall size of the parent is larger and has a looser more open habit. The internodes on the new growth range from 3.5 cm to 6.5 cm exhibiting a more sprawling plant. Whereas, my selection has an overall denser and more compact habit with internode length on new growth to a maximum of 2.5 cm.

The growth rate on my selection is slower, achieving a saleable 6" size from a 2" pot in 6 months in the warmer months to 8 months in the cooler months. Whereas, the parent *Lantana sellowiana* will grow to a comparable size in 4 months in the warmer months and 6 months in the cooler months. My selection exhibits a 50% slower growth rate.

The ultimate size of *Lantana sellowiana* cultivar 'Mongen' is approximately 25 cm tall and 65 cm wide. The parent selection will achieve a height of approximately 50 cm and spread to 180 cm wide.

The parent plant exhibits a darker leaf color of Greer Group 137A on the upper leaf surface and a lighter grey green. Yellow Green 146B, on the under leaf surface. My new selection exhibits this lighter grey green, Yellow Greer 146B on the upper leaf surface.

Flower color and size appear similar. The parent plant has more numerous inflorescences when compared to my new selection at a similar age.

The parent selection blooms most heavily summer to fal then sporadically throughout the year. *Lantana sellowiana* cultivar 'Mongen' blooms mostly summer to fall with very few blooms the rest of the year. *Lantana camara* cultivar 'Variegata' (unpatented) is another selection which as a reversed variegated foliage of inner blotch Green Group 137C and outer margin of Yellow Green Group 154D. However, cv. 'Variegata' has a more shrubby habit and bloom color is a bright golden color, Yellow 13A. The foliage size is also larger in size 4 to 5 cm in length, 3 cm in width. *Lantana sellowiana* cultivar Mongen was discovered as a branch mutation from *Lantana sellowiana* so we are assured this is a species and no hybridity is involved.

BRIEF DESCRIPTION OF ILLUSTRATION

The accompanying photograph exhibits the floral and vegetative characteristics of my new selection. The color is depicted as nearly true as possible.

BOTANICAL DESCRIPTION

Below is a detailed description of *Lantana sellowiana* cultivar 'Mongen', the color terminology is from The Royal Horticultural Colour Chart. Measurements and descriptions are based on 3 random samples of container plants grown in Azusa, Calif. taken in July of 1997. Phenotypic appearance may vary under different environmental and cultural conditions.

Overall habit. Subshrub or groundcover dense mounding growth, not as vigorous as parent plant, evergreen to 20° F. (−7° C.), deciduous in lower temperatures to 10° F. (−12° C.).

Overall size: Mature specimen likely to remain under 25 cm tall and spreading not to exceed 60 cm.

Tolerance to cold temperatures: Plant is evergeen to approximately 20° F. (−7° C.) temperatures. Plant will likely survive winters down to 10° F. (−12° C.) however, at this temperature the top growth is completely killed back, roots will survive and new shoots will respout from the ground each spring.

'olerance to high temperatures: *Lantana sellowiana* 'Mongen' is able to withstand temperatures of 100° F. to 115° F. My new selection though heat tolerant should be provided light shade to protect the variegated foliage from possible burn.

'olerance to drought: Both the parent of my new selection and my selection are highly recommended as a water wise and drought tolerant landscape plant.

'lowers:

*Bloom season.*—Free flowering throughout the year in southern California heavily summer through fall.

*Arrangement.*—Flowers complete, sessile in axils of the involucre, in peducled heads.

*Peduncle.*—My selection is typically less than the 5.0 cm. in length with color Greyed-Purple Group 187A. In the species, *Lantana sellowiana* peduncle length is typically longer than 5.0 cm.

*Number per inflorecence.*—10–20 flowers.

*Corolla width.*—0.8 cm±0.2 cm similar to parent.

*Corolla length.*—1.0 cm±0.2 cm similar to parent.

*Corolla shape.*—Sympetalous, irregularly 4–5 lobed. Tube slender.

*Inflorescence width.*—Average 2.0 cm±0.4 cm.

'lower bud: Small, sessile in axils of the bracts, numerous up to 20 per head. Flower heads in bud stage are 0.5 cm long and wide enlarging with maturity.

*Inflorescence length inclusive of involucre bracts.*—Average 1.5 cm±0.3 cm.

*Corolla color.*—Purple-Violet Group 81B, 81C, and 81D on upper and lower side of lobes. Occasionally some flowers exhibit a white throat, White Group 155A, no larger than 3 mm in diameter with a central eye of Yellow-Orange Group 20B.

*Lobe size.*—3–5 mm in length and 3–6 mm in width.

*Lobe apex.*—Rounded.

*Lobe margin.*—Entire, slightly revolute.

*Color of involucre bracts.*—Variegated similar to foliage Yellow Group 8C, Yellow-Green Group 146B.

*Shape of involucre bracts.*—Narrow elliptic, the outer 5–6 are broad ovate and puberulent.

*Length of involucre bracts.*—Not exceeding more than half of the slender pubescent corolla tube.

Foliage:

*Arrangement.*—Opposite.

*Surface.*—Deep reticulated veination.

*Shape.*—Apex: accuminate to acute. Base: oblique. Overall: ovate.

*Margins.*—Crenate.

*Size.*—Length varies 3.0 cm–2.0 cm, width varies 2.0 cm to 1.5 cm.

*Petiole.*—3 to 5 mm.

*Color.*—Normally upper surface of foliage is a Yellow-Green Group 146B irregular central leaf blotch of color surrounded by irregular Yellow Group 8C to the margins. The lower surface is surrounded by the same color of irregular Yellow Group 8C, however the irregular central blotch is Green Group 138B.

*Texture.*—Slightly coriaceous with deep reticulated veination.

*Pubescense.*—Lightly puberulent on upper leaf surface; puberulent on lower leaf surface.

Reproductive organs

*Stamens.*—4 in number, didynamous attached midway in the tube, included in the tube.

*Anthers.*—Greyed-Orange Group 174A, 0.05 mm in length.

*Stigma.*—One, Yellow-Green Group 150B.

*Style.*—One, Yellow-Green Group 150D.

*Ovaries.*—2-celled.

*Fruit.*—Not observed.

Disease and pest resistance: This selection is typically free of pests and diseases with resistance similar to parent plant.

I claim:

1. A new and distinct Lantana plant as substantially shown and described herein, that is characterized particularly as a novelty by the unique combination of variegated leaves and slower growth habit.

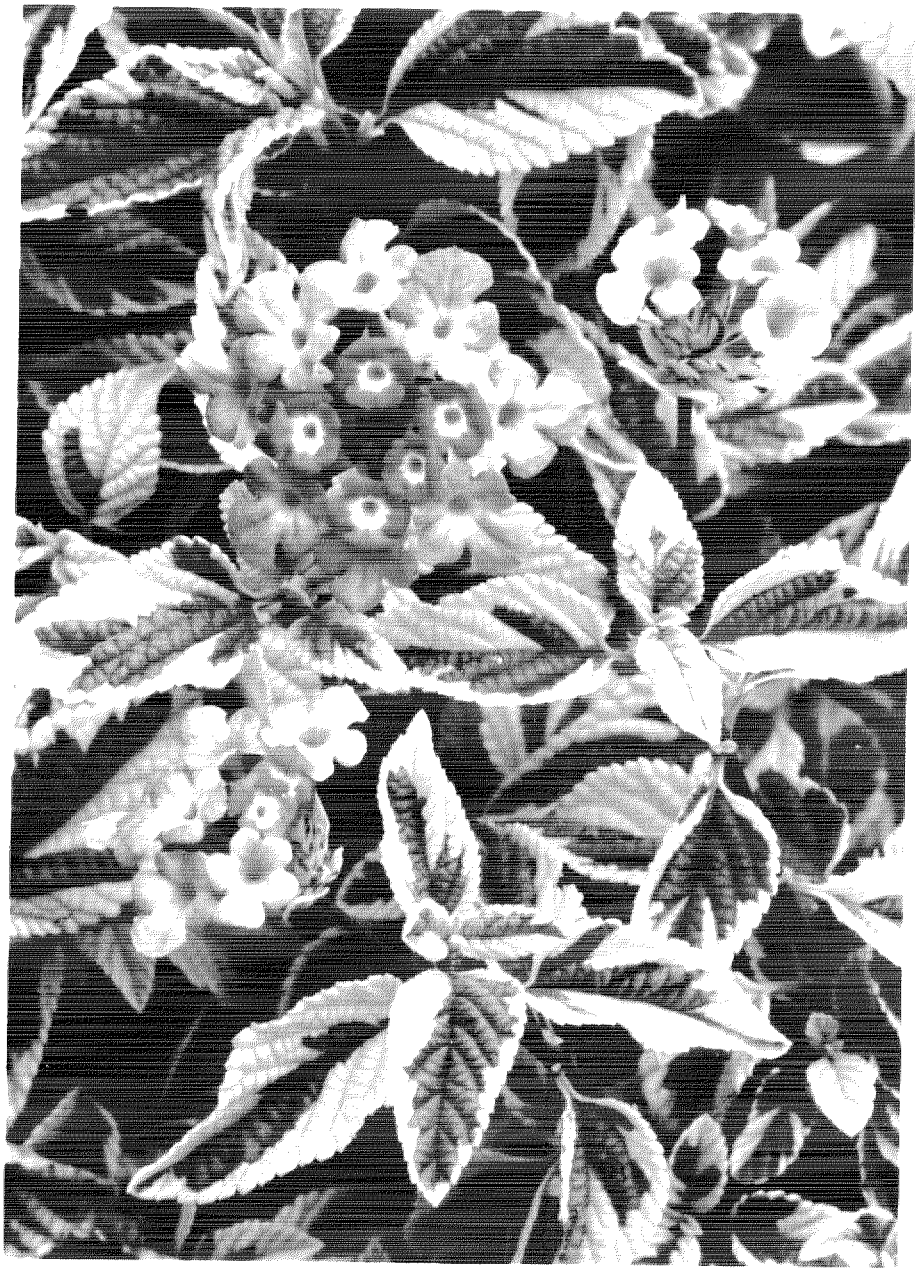

* * * * *